(12) United States Patent
Gallou et al.

(10) Patent No.: US 7,268,211 B2
(45) Date of Patent: Sep. 11, 2007

(54) REMOVAL OF RUTHENIUM BY-PRODUCT BY SUPERCRITICAL FLUID PROCESSING

(75) Inventors: Fabrice Gallou, Danbury, CT (US); Said Saim, New Milford, CT (US); Nathan K. Yee, Danbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 219 days.

(21) Appl. No.: 11/006,475

(22) Filed: Dec. 7, 2004

(65) Prior Publication Data

US 2005/0154186 A1 Jul. 14, 2005

Related U.S. Application Data

(60) Provisional application No. 60/527,668, filed on Dec. 8, 2003.

(51) Int. Cl.
*C07K 5/12* (2006.01)
*C07D 245/00* (2006.01)
*C07F 15/00* (2006.01)

(52) U.S. Cl. .................. 530/317; 556/21; 556/22; 548/101; 540/460; 34/329; 34/337; 570/190; 570/211

(58) Field of Classification Search ................ 530/317; 540/460; 34/329, 337; 556/21, 22; 548/101; 570/190, 211
See application file for complete search history.

(56) References Cited

U.S. PATENT DOCUMENTS

| | | | |
|---|---|---|---|
| 5,811,515 A | 9/1998 | Grubbs et al. | |
| 5,840,820 A | 11/1998 | DeSimone et al. | |
| 6,306,987 B1 | 10/2001 | Van Der Schaaf et al. | |
| 6,323,180 B1 | 11/2001 | Llinas-Brunet et al. | |
| 6,608,027 B1 | 8/2003 | Tsantrizos et al. | |
| 7,148,347 B2 | 12/2006 | Brandenburg et al. | |
| 2003/0181363 A1 | 9/2003 | Llinas-Brunet et al. | |
| 2003/0224977 A1 | 12/2003 | Llinas-Brunet et al. | |
| 2004/0248779 A1 | 12/2004 | Dersch et al. | |
| 2005/0049187 A1 | 3/2005 | Bradenburg et al. | |
| 2005/0075279 A1 | 4/2005 | Llinas et al. | |
| 2005/0080005 A1 | 4/2005 | Llinas-Brunet et al. | |
| 2005/0119453 A1* | 6/2005 | Brenner et al. | 530/317 |
| 2005/0215423 A1* | 9/2005 | Brenner et al. | 502/111 |
| 2006/0063915 A1* | 3/2006 | Gallou et al. | 530/317 |

FOREIGN PATENT DOCUMENTS

| | | |
|---|---|---|
| WO | 0009543 | 2/2000 |
| WO | 0009558 | 2/2000 |
| WO | WO 02/081414 A2 | 10/2002 |
| WO | 2004089974 A1 | 10/2004 |
| WO | 2004092203 A2 | 10/2004 |

OTHER PUBLICATIONS

Fuerstner, Alois, et al; Olefin Metathesis in Compressed Carbon Dioxide, Angew Chem. Int. Ed. Engl. 1997, 36 No. 22—XP 002102059.
U.S. Application entitled Ring-Closing Metathesis Process in Supercritical Fluid, filed Sep. 9, 2005 and accorded U.S. Appl. No. 11/222,882.
W. Leitner, Homogeneous catalysts for application in supercritical carbon dioxide as a 'green' solvent; C.R. Acad. Sci. Paris, Serie llc, Chimie/ Chemistry 3 (2000), 595-600.
Furstner, A., Olefinmetathese in Komprimiertem Kohlendioxid; Angew. Chem., 1997, 109, 2562.
Furstner, A., et al., Olefin Metathesis in Supercritical Carbon Dioxide; J. Amer. Chem. Soc., 2001, 123, 9000-9006.
Grubbs and Chang; Recent Advances in Olefin Metathesis and Its Application in Organic Sythesis; Tetrahedron report number 448; vol. 54; 1998; pp. 4413-4450; Elsevier Science Ltd.
Fuerstner; Olefin Metathesis and Beyond; Angewandte Chemie Int. Ed.; 2000; vol. 39; pp. 3012-3043.
Maynard and Grubbs; Purification Technique for the Removal of Ruthenium from Olefin Metathesis Reaction Products; Tetrahedron Letters; vol. 40; 1999; pp. 4137-4140; Elsevier Science Ltd.
Paquette, et al; A Convenient Method for Removing All Highly-Colored Byproducts Generated during Olefin Metathesis Reactions; Organic Letters; vol. 2, No. 9; 2000; pp. 1259-1261.

(Continued)

*Primary Examiner*—Porfirio Nazario-Gonzalez
(74) *Attorney, Agent, or Firm*—Michael P. Morris; Mary-Ellen M. Devlin; Philip I. Datlow

(57) ABSTRACT

A process for removing ruthenium or ruthenium-containing compounds from a reaction mixture comprising a compound of the following formula I in an organic solvent using supercritical fluid processing techniques:

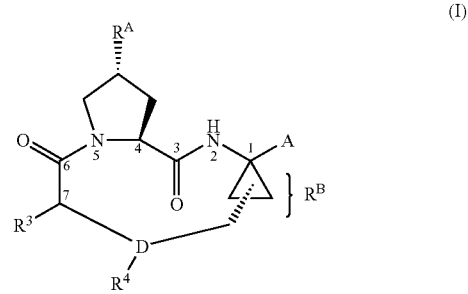

(I)

wherein $R^A$, $R^3$, $R^4$, D and A are as defined herein. This invention has particular application for removing ruthenium-containing catalyst and ruthenium-containing catalyst by products from reaction mixtures that result from ring-closing olefin metathesis (RCM) reactions.

30 Claims, No Drawings

OTHER PUBLICATIONS

Ahn, et al; A Convenient Method for the Efficient Removal of Rithenium Byproducts Generated during Olefin Metathesis Reactions; Organic Letters; vol. 3, No. 9; 2001; pp. 1411-1413.

Cho, et al; An Efficient Method for Removal of Ruthenium Byproducts from Olefin Metathesis Reactions; Organic Letters; vol. 5, No. 4; 2003; pp. 531-533.

Jafarpour, et al; Preparation and Activity of Recyclable Polymer-Supported Ruthenium Olefin Metathesis Catalysts; Organometallics; vol. 21; 2002; pp. 671-679.

Jafarpour, et al; Indenylidenep-Imidazolylidene Complexes of Ruthenium as Ring-Closing Metathesis Catalysts; Organometallics; vol. 18; 1999; pp. 5416-5419.

Dias and Grubbs; Synthesis and Investigation of Homo- and Heterobimetallic Ruthenium Olefin Metathesis Catalysts Exhibiting Increased Activities; Organometallics; vol. 17; 1998; pp. 2758-1767.

Sanford, et al; Mechanism and Activity of Ruthenium Olefin Metathesis Catalysts; Journal of American Chemical Society; vol. 123; 2001; pp. 6543-6554.

Kingsbury, et al; A Recyclable Ru-Based Metathesis Catalyst; Journal of American Chemical Society; vol. 121; 1999; pp. 791-799.

Huang, et al; Olefin Metathesis-Active Ruthenium Complexes Bearing a Nucleophilic Carbene Ligand; Journal of American Chemical Society; vol. 121; 1999; pp. 2674-2678.

Van Veldhuizen, et al; A Recyclable Chiral Ru Catalyst for Enantioselective Olefin Metathesis. Efficient Catalytic Asymmetric Ring-Opening/Cross Metathesis in Air; Journal of American Chemical Society; vol. 124; 2002; pp. 4954-4955.

Men, et al; Substrate Synthesis and Activity Assay for MurG; Journal of American Chemical Society; vol. 120; 1998; pp. 2484-2485.

Dias, et al; Well-Defined Ruthenium Olefin Metathesis Catalysts: Mechanism and Activity; Journal of American Chemical Society; vol. 119; 1997; pp. 3887-3897.

Schwab; Synthesis and Applications of RUC12(=CHR')(PRe)2: The Influence of the Alkylidene Moiety of Metathesis Activity; Journal of American Chemical Society; vol. 118; 1996; pp. 100-110.

Miller, et al; Application of Ring-Closing Metathesis to the Sythesis of Ridified Amino Acids and Peptides; Journal of American Chemical Society; vol. 118; 1996; pp. 9606-9614.

Fu and Grubbs; The Application of Catalytic Ring-Closing Olefin Metathesis to the Synthesis of Unsaturated Oxygen Heterocycles; Journal of American Chemical Society; vol. 114; 1992; pp. 5426-5427.

Kirkland, et al; Ring-Closing Metathesis in Methanol and Water; Journal of Organic Chemistry; vol. 63; 1998; pp. 9904-9909.

Ulman and Grubbs; Ruthenium Carbene-Based Olefin-Metathesis Initiators: Catalyst Decomposition and Longevity; Journal of Organic Chemistry; vol. 64; 1999; pp. 7202-7207.

Hinderling, et al; Olefin Metathesis of a Ruthenium Carbene Complex by Electrospray Ionization in the Gas Phase; Angewandte Chemie International Edition; vol. 37; No. 19; 1998; pp. 2685-2689.

Grissom and Huang; Low-Temperature Tandem Enyne Allene Radical Cyclizations: Efficient Synthesis of 2,3-Dihydroindenes from Simple Enediynes; Angewandte Chemie International Edition; vol. 34; No. 18; 1995; pp. 2037-2039.

Grela, et al; A Highly Efficient Ruthenium Catalyst for Metathesis Reactions; Angewandte Chemie International Edition; vol. 41; No. 21; 2002; pp. 4038-4040.

Rano and Chapman; Solid Phase Synthesis of Aryl Ethers Via the Mitsunobu Reaction; Tetrahedron letters; vol. 36, No. 22; 1995; pp. 3789-3792.

Krchnak, et al; Polymer-Supported Mitsunobu Ether Formation and its Use in Combinatorial Chemistry; Tetrahedron Letters; vol. 36, No. 35; 1995; pp. 6193-6196.

Mitsunobu; The Use of Diethyl Azodicarboxylate and Triphenylphosphine in Synthesis and Transformation of Natural Products; Synthesis; 1981; pp. 1-28; published by Georg Thieme Verlag; Stuttgart and New York.

\* cited by examiner

REMOVAL OF RUTHENIUM BY-PRODUCT BY SUPERCRITICAL FLUID PROCESSING

CROSS-REFERENCE TO RELATED APPLICATIONS

This application claims benefit from U.S. Provisional Application No. 60/527,668, filed Dec. 8, 2003.

BACKGROUND OF THE INVENTION

1. Technical Field

This invention relates in general to a process for removing ruthenium or ruthenium-containing compounds from reaction mixtures using supercritical fluid processing techniques. This invention has particular application for removing ruthenium-containing catalyst and ruthenium-containing by products from reaction mixtures resulting from ring-closing olefin metathesis (RCM) reactions.

2. Background Information

The olefin metathesis reaction has become an important method in organic synthesis (see for example R. H. Grubbs and S. Chang, Tetrahedron 1998, 54, 4413; D. L. Wright, Curr. Org. Chem., 1999, 3, 211; A. Fürstner, Angew. Chem. Int. Ed. Engl., 2000, 39, 3012). In this reaction, two alkenes are joined to form a new olefin having one carbon from each original alkene. The reaction takes place in the presence of a metal carbene catalyst.

In general there are three types of olefin metathesis reactions: ring-opening metathesis polymerization, acyclic cross metathesis and ring-closing metathesis (RCM). The RCM is an effective means to prepare cyclic compounds from a diolefin (FIG. 1).

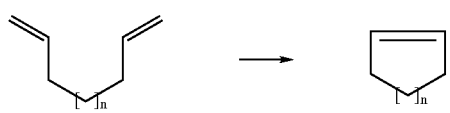

FIG. 1

The reaction can be used to prepare various sized rings and it tolerates heteroatoms and various functional groups in the molecule. Popular catalytic reactive species for olefin metathesis reactions include ruthenium and molybdenum carbenes generated from precatalyst complexes such as the ruthenium vinylidene complex shown in FIG. 2 (Grubb's catalyst, G. Fu and R. H. Grubbs, J. Am. Chem. Soc. 1992, 114, 5426).

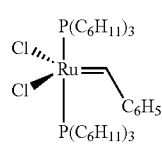

FIG. 2

While providing a valuable tool for the synthesis of complex organic molecules, the olefin metathesis reaction does have some complications. Use of the catalyst may result in formation of potentially undesirable, highly colored by-products that are difficult to remove. The presence of these by-products is not acceptable in pharmaceuticals. Often several chromatographic steps are required to remove such by-products. Furthermore, if the impurities are not removed they can cause further problems including decomposition and double-bond migration.

A number of techniques have been reported to remove ruthenium by-products from olefin metathesis reaction mixtures. One technique uses a water-soluble phosphine ligand to coordinate with the ruthenium and facilitate removal by aqueous extraction (H. D. Maynard and R. H. Grubbs, Tetrahedron Letters 1999, 40, 4137). Another method reported in the literature involves stirring for several hours with lead tetraacetate to oxidize the ruthenium by-products followed by filtration through silica gel (L. A. Paquette et al., Org. Lett. 2000, 2, 1259). A third method involves treatment of the crude reaction mixture with triphenylphosphine oxide or DMSO followed by a chromatographic filtration through silica gel (Y. M. Ahn et al., Org. Lett. 2001, 3, 1411). Treatment of the reaction mixture with silica gel and activated carbon followed by chromatography on silica gel is described in another method (J. H. Cho and B. M. Kim, Org. Lett., 2003, 5, 531).

However, each of the above techniques still suffer from disadvantages that make them undesirable for large-scale preparations or for pharmaceuticals. They introduce new, potentially toxic entities which also may not be chemically compatible with the desired reaction product that is being purified. The water soluble ligand is expensive and needs to be used in large excess relative to the by-products being removed. Each method requires either extractions or chromatographic filtrations that are both tedious and add to the processing time. Furthermore, these methods chemically modify the ruthenium catalyst which complicates or eliminates the possibility of catalyst recycling.

The macrocyclic compounds of the following formula (I) and methods for their preparation are known from: Tsantrizos et al., U.S. Pat. No. 6,608,027 B1; Llinas Brunet et al, U.S. Application Publication No. 2003/0224977 A1; Llinas Brunet et al, U.S. application Ser. No. 10/686,755, filed Oct. 16, 2003; Llinas Brunet et al, U.S. application Ser. No. 10/945,518, filed Sep. 20, 2004; Brandenburg et al., U.S. application Ser. No. 10/818,657, filed Apr. 6, 2004 and WO 2004/092203; Samstag et al., U.S. application Ser. No. 10/813,344, filed Mar. 30, 2004, and WO 2004/089974, all of which are herein incorporated by reference:

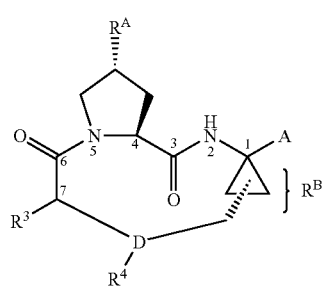

wherein
R⁴ is a leaving group or a group of formula II

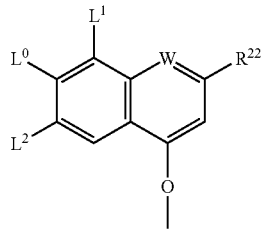

(II)

W is CH or N,
L⁰ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$,
wherein each $R^{23}$ is independently H, $C_{1-6}$ alkyl or $C_{3-6}$ cycloalkyl;
$L^1$, $L^2$ are each independently H, halogen, $C_{1-4}$alkyl, —O—$C_{1-4}$alkyl, or —S—$C_{1-4}$alkyl (the sulfur being in any oxidized state); or
$L^0$ and $L^1$ or
$L^0$ and $L^2$ may be covalently bonded to form together with the two C-atoms to which they are linked a 4-, 5- or 6-membered carbocyclic ring wherein one or two (in the case of a 5- or 6-membered ring) —$CH_2$— groups not being directly bonded to each other, may be replaced each independently by —O— or $NR^a$ wherein $R^a$ is H or $C_{1-4}$alkyl, and wherein said ring is optionally mono- or di-substituted with $C_{1-4}$ alkyl;
$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;
said cycloalkyl, aryl or Het being substituted with $R^{24}$,
wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$; or NH—C(O)—NH—$R^{25}$, wherein each $R^{25}$ is independently: H, $C_{1-6}$ alkyl or $C_{3-6}$ cycloalkyl;
or $R^{24}$ is NH—C(O)—$OR^{26}$ wherein $R^{26}$ is $C_{1-6}$ alkyl or $C_{3-6}$ cycloalkyl;
$R^3$ is hydroxy, $NH_2$, or a group of formula —NH—$R^9$, wherein $R^9$ is $C_6$ or $_{10}$ aryl, heteroaryl, —C(O)—$R^{20}$, —C(O)—$NHR^{20}$ or —C(O)—$OR^{20}$, wherein $R^{20}$ is $C_{1-6}$ alkyl or $C_{3-6}$ cycloalkyl;
D is a 5 to 10 atom saturated or unsaturated alkylene chain optionally containing one to three heteroatoms independently selected from: O, S or N—$R^{27}$, wherein $R^{27}$ is H, $C_{1-6}$alkyl, $C_{3-6}$cycloalkyl or $C(O)R^{28}$, wherein $R^{28}$ is $C_{1-6}$alkyl, $C_{3-6}$cycloalkyl or $C_6$ or $_{10}$ aryl;
R⁴ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
A is an amide of formula —C(O)—NH—$R^{11}$, wherein $R^{11}$ is selected from the group consisting of: $C_{1-8}$ alkyl, $C_{3-6}$ cycloalkyl, $C_6$ or $_{10}$ aryl, $C_{7-16}$ aralkyl, or $SO_2R^{54}$ wherein $R^{54}$ is $C_{1-8}$ alkyl, $C_{3-7}$ cycloalkyl, $C_{1-6}$ alkyl-$C_{3-7}$ cycloalkyl;
or A is a carboxylic acid or a pharmaceutically acceptable salt or ester thereof.

The compounds of formula (I) are disclosed in the above-mentioned patent documents as being active agents for the treatment of hepatitis C virus (HCV) infections, or as intermediates useful for the preparation of such anti-HCV agents as described therein, and are prepared therein via RCM of an acyclic diolefin using ruthenium-based catalysts. In these previous processes, the cyclized product is purified by either column chromatography or using a scavenging agent, such as trishydroxymethylphosphine (THP), to effect removal of the ruthenium by-product from the reaction mixture. However, such processes suffer from the same disadvantages as described above, making them undesirable for large-scale preparations or for pharmaceuticals.

We describe herein a method for removing the ruthenium catalyst by-products from the cyclized product of formula (I) that does not suffer from the disadvantages described above. The process of the present invention employs supercritical fluid processing as a technique to separate the macrocyclic product of formula (I) from the ruthenium catalyst by-products.

It has been reported that supercritical carbon dioxide may be used as a versatile reaction medium for conducting certain olefin metathesis reactions, and in the case of ring-closing olefin metathesis (RCM) reactions, the solubility properties of the supercritical carbon dioxide may be exploited to isolate the low molecular weight RCM products from the ruthenium complex via selective supercritical fluid extraction (Furstner et al., *J. Am. Chem. Soc.*, 2001, 123, 9000; W. Leitner, *C. R. Acad. Sci. Paris, Serie IIc, Chimie*, 2000, 3, 595; Furstner et al., *Angew. Chem.*, 1997, 109, 2562, and *Angew. Chem. Int. Ed. Engl.*, 1997, 36, 2466). However, although numerous examples are provided using lower molecular weight RCM products, there is no disclosure or suggestion that such technique would be effective to extract and separate higher molecular weight RCM products, such as the compounds of formula (I), from the ruthenium by-products.

BRIEF SUMMARY OF THE INVENTION

The present invention is directed to a process for removing ruthenium or ruthenium-containing compound from a mixture comprising:
(i) a compound of formula (I) as previously set forth;
(ii) an organic solvent; and
(iii) ruthenium or ruthenium-containing compound;
said process comprising:
(1) exposing said mixture to a sufficient quantity of pressurized gaseous fluid to form a fluid solution in which the compound of formula (I) and organic solvent are substantially soluble but said ruthenium or ruthenium-containing compound is substantially insoluble such that particles of the ruthenium or ruthenium-containing compound precipitate out of said solution;
(2) introducing the fluid solution into a lower pressure region to expel at least some of said gaseous fluid from the fluid solution and obtain an organic solvent solution comprising the compound of formula (I) and the organic solvent;
(3) optionally repeating steps (1) and (2) one or more times using the organic solvent solution obtained in step (2) as the mixture to be exposed in step (1) to said pressurized gaseous fluid; and
(4) optionally recovering the compound of formula (I) from the organic solvent solution.

Depending upon the conditions employed, this process can be used to significantly reduce the level of ruthenium in the recovered compound of formula (I), in some cases to less than about 60 ppm.

DETAILED DESCRIPTION OF THE INVENTION

1. Definitions

All terms as used herein in this application, unless otherwise stated, shall be understood in their ordinary meaning as known in the art. Other more specific definitions for certain terms as used in the present application are as set forth below:

By the term "about" with respect to a recited value is meant ±20% of the recited value, preferably ±10%, more preferably ±5%, even more preferably ±1%. When the term "about" is used in relation to a range of values, the term "about" is intended to qualify each recited end-point of the range. For example, the phrase "about 30 to 150° C." is equivalent to "about 30 to about 150° C.".

By "gaseous fluid", or "supercritical fluid" is meant (1) a fluid or mixture of fluids that is gaseous under atmospheric conditions and that has a moderate critical temperature (i.e., ≦200° C.), or (2) a fluid that has previously found use as a supercritical fluid. Examples of gaseous fluids include those that have a critical temperature of less than about 200° C. and a critical pressure of less than about 689 bar. Specific examples include carbon dioxide, nitrous oxide, trifluoromethane, ethane, ethylene, propane, sulfur hexafluoride, propylene, butane, isobutane, pentane, and mixtures thereof.

By the term "processing conditions" is meant the specific conditions under which a process of the present invention is run.

By the term "substantially soluble", e.g., with respect to the solubility of the compound of formula (I) and the organic solvent in the fluid solution, is meant that under selected processing conditions the organic solvent and the compound of formula (I) can be solubilized to a level of at least about 95%, more preferably at least about 99% in the fluid solution.

By the term "substantially insoluble", e.g., with respect to the solubility of the ruthenium or ruthenium-containing compound in the fluid solution, is meant that under selected processing conditions the ruthenium or ruthenium-containing compound should be no more than about 10% by weight soluble, more preferably no more than about 5% by weight soluble, even more preferably no more than about 1% by weight soluble in the fluid solution. It is preferable that under the selected processing conditions the ruthenium or ruthenium-containing compound is essentially completely insoluble in the fluid solution.

The following chemicals may be referred to by these abbreviations:

| Abbreviation | Chemical Name |
| --- | --- |
| Boc | Tert-butoxylcarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DIPEA | Diisopropylethylamine or Hünigs-Base |
| DMAP | Dimethylaminopyridine |
| DMF | N,N-Dimethylformamide |
| DMSO | Dimethylsulfoxide |

-continued

| Abbreviation | Chemical Name |
| --- | --- |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiinide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |
| HOAT | 1-Hydroxy-7-azabenzotriazole |
| HOBT | 1-Hydroxybenzotriazole |
| MCH | Methylcyclohexane |
| MIBK | 4-Metyl-2-pentanone |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |
| THP | Trishydroxymethylphosphine |

II. Steps of the Process

Step 1: Exposure of the Mixture to Gaseous Fluid

In this first step, a mixture containing a macrocyclic compound of formula (I), ruthenium or ruthenium-containing compound and an organic solvent is exposed to a pressurized gaseous fluid to form a fluid solution. In one embodiment, the mixture to be exposed is a reaction mixture obtained from a ring-closing olefin metathesis (RCM) reaction of the corresponding acyclic diene compound dissolved in an organic solvent and catalyzed by a ruthenium-based catalyst. This RCM reaction generally results in a reaction mixture comprising a macrocyclic formula (I) compound, ruthenium catalyst and ruthenium catalyst by-products dissolved in an organic solvent. In this embodiment, it is this RCM reaction mixture which may be exposed to the pressurized gaseous fluid to effect a supercritical fluid extraction and separation of the macrocyclic product of formula (I) dissolved in organic solvent from the ruthenium and ruthenium-containing catalyst and catalyst by-products. This extraction is possible due to the differential solubilities of the macrocyclic compound of formula (I), organic solvent, ruthenium and ruthenium-containing catalyst and catalyst by-products in the resulting fluid solution that can be achieved under appropriate processing conditions.

Generally, the reaction mixture is exposed to a sufficient quantity of pressurized gaseous fluid such that a fluid solution is formed in which the compound of formula (I) and organic solvent are substantially soluble but the ruthenium or ruthenium-containing compound is substantially insoluble such that the compound of formula (I) remains substantially in solution while the ruthenium and ruthenium compounds precipitate out of the fluid solution, thus effecting the desired separation. The amount of gaseous fluid used should be sufficient to cause the resulting fluid solution to be saturated with the ruthenium compounds, resulting in the precipitation of the ruthenium compounds out of the solution. The type and amount of gaseous fluid and the processing conditions to be employed in any particular case can be readily determined by a person skilled in field of supercritical fluid processing techniques with reference to the description and examples set forth herein and known techniques.

In particular embodiments, the mixture may be exposed to the pressurized gaseous fluid by either (a) introducing the gaseous fluid into a vessel containing the mixture (generally a batch-type process) or (b) introducing the mixture into a vessel containing the gaseous fluid, for example, by injecting the mixture into the vessel containing the gaseous fluid (generally used for continuous processing). When introducing the pressurized gaseous fluid into a vessel containing the mixture, any of the conventional conditions (i.e., temperature, pressure, fluid flow rate, precipitation vessels, nozzle variations, etc) that are commonly used in the art for Gas Anti-Solvent Recrystallization (GAS) processing can be employed. When introducing the mixture into a vessel containing a pressurized gaseous fluid any of the conventional conditions (i.e., temperature, pressure, fluid flow rates, precipitation vessels, nozzle variations, etc) that are commonly used in the art for Supercritical Fluid Antisolvent (SAS) processing can be employed. See Saim et al. U.S. Patent Application Publication No. 2003/0066800 A1, herein incorporated by reference, for a description of such techniques that may be adapted for the present invention. The processing conditions therein described can of course be adjusted by the skilled technician over wide ranges to obtain the desired optimum performance in the present inventive method.

In continuous processing, the mixture is typically introduced into a vessel containing the pressurized gaseous fluid, for example, by continuous injection of the mixture at an appropriate flow rate into a vessel containing pressurized gaseous fluid at an appropriate pressure level to effect the extraction of the formula (I) compound and organic solvent and precipitation of ruthenium-containing compounds. Typically, there is simultaneous and continuous flow of both the mixture and gaseous fluid into the vessel at appropriate relative flow rates. The ratio of mixture molar flow rate to gaseous fluid molar flow rate should preferably be in the range of about 0.001 to 0.2, more preferably in the range of about 0.01 to 0.05. Pressure, temperature, gaseous fluid molar flow rate and mixture molar flow rate should preferably be such that the fluid solution in the precipitation vessel is homogeneous. The nozzle through which the mixture may be introduced into the precipitation vessel can be, for example, an orifice nozzle, a capillary nozzle, an ultrasonic nozzle, or a coaxial nozzle, e.g. the type employed in a SEDS method, as discussed previously. The mixture may alternatively be introduced through a regular flow line or orifice with no spray atomization capability.

The gaseous fluid employed in the inventive method includes, for example, any gaseous fluid that is commonly employed in conventional supercritical fluid processes. Examples of gaseous fluids that may be used include those that have a critical temperature of less than about 200° C. and a critical pressure of less than about 689 bar. Specific examples include carbon dioxide, nitrous oxide, trifluoromethane, ethane, ethylene, propane, sulfur hexafluoride, propylene, butane, isobutane, pentane, and mixtures thereof. A preferred gaseous fluid is carbon dioxide.

Preferred process conditions for the exposure step are as follows: The exposure is preferably conducted at a temperature in the range of about 0.8 to 2.0 times the critical temperature of the gaseous fluid in degrees Kelvin, and at a pressure in the range of about 0.5 to 30 times the critical pressure of the gaseous fluid; more preferably at a temperature in the range of about 1.0 to 1.1 times the critical temperature of the gaseous fluid in degrees Kelvin, and at a pressure in the range of about 1 to 10 times the critical pressure of the gaseous fluid.

In a specific embodiment, the gaseous fluid is carbon dioxide and the exposure step is conducted at a temperature of about 30 to 150° C. and at a pressure of about 74 to 500 bar.

It is desirable that the final fluid solution resulting from the exposure of the mixture to the gaseous fluid should contain a high level of gaseous fluid. Preferably, the amount of gaseous fluid in the resulting fluid solution is in the range of about 50 to 99.9%, more preferably about 80 to 99.9%.

In another embodiment, the exposure step may be conducted in the presence of a bed of carrier material capable of retaining precipitated particles of ruthenium or ruthenium-containing compound, which may be effective in further reducing the amount of ruthenium or ruthenium compound in the extracted compound of formula (I). The carrier material used in the inventive method can be selected from any material that would be effective in retaining the precipitated particles of ruthenium or ruthenium-containing compound. Examples of carriers that can be used include lactose, including hydrated forms thereof, dextrose, sucrose, starch, polyethylene glycol, PVP, polyvinyl alcohol, lecithin, microcrystalline cellulose, hydroxypropyl methyl cellulose, calcium carbonate, dicalcium phosphate, calcium triphosphate, magnesium carbonate, sodium chloride and diatomaceous earth. The bed of carrier material is preferably maintained in a mixed state, for example, by stirring the bed using one or more rotating mixing devices. Speeds in the range of 50 to 3,000 RPM are preferred.

The organic solvent that may be used is any organic solvent in which the compound of formula (I) is substantially soluble and which, itself, is substantially soluble in the gaseous fluid and the resulting fluid solution under selected processing conditions. In one embodiment, this organic solvent may be the organic solvent employed in the RCM reaction to prepare the macrocyclic compound of formula (I), as discussed previously. Examples of organic solvents that may be used include toluene, dichloromethane, THF, dioxane, ethyl acetate, tert-butyl acetate, methyl-tert-butyl ether, methanol, water, and mixtures thereof.

The ruthenium or ruthenium-containing compound that is present in the mixture to be extracted is typically the ruthenium catalyst used in the RCM reaction and any ruthenium containing by products in the reaction mixture resulting from the RCM reaction.

Step 2: Gaseous Fluid Venting

After precipitation of the ruthenium or ruthenium-containing compounds from the fluid solution, the fluid solution is introduced into a lower pressure region to expel at least some of the gaseous fluid from the solution, resulting in an organic solvent solution containing the compound of formula (I) in the organic solvent. The fluid solution flows out of the precipitation vessel and is then expanded at a reduced pressure level to separate the gaseous fluid from the organic solvent solution. The organic solvent solution can be recovered in a cold trap and the gaseous fluid vented or recycled into the process. Typically, the pressure in the lower pressure region is at about ambient pressure.

Step 3: Optional Process Recycling

Optionally, the first two steps of exposure of the mixture to gaseous fluid and gaseous fluid venting may be repeated one or more times using the organic solvent solution obtained after the first venting step as the mixture to be again exposed to the gaseous fluid. This recycling may be useful for further reducing the ruthenium content in the product of formula (I). In one embodiment, the procedure can be repeated one or two times.

Step 4: Optional Recovery of Formula (I)

Optionally, the compound of formula (I) having the reduced ruthenium content may be recovered from the organic solvent solution, for example, by distillation or precipitation using conventional techniques. The recovered compound of formula (I) could then be formulated for the preparation of an anti-HCV pharmaceutical composition or used as an intermediate to prepare anti-HCV agents, as would be understood from the numerous patent documents cited hereinabove under Background Information.

The process of the present invention has shown to significantly reduce the level of ruthenium in the recovered compound of formula (I) to more acceptable levels for pharmaceutical processing. In particular embodiments, the level of ruthenium in the recovered compound of formula (I) is less than about 10000 ppm, preferably less than about 1000 ppm, preferably less than about 300 ppm, preferably less than about 100 ppm, preferably less than about 60 ppm. The processing conditions herein described can be adjusted by the skilled technician to obtain the desired optimum performance and reduced ruthenium levels possible with the present inventive method.

III. The Compounds of Formula (I)

Additional more specific embodiments of the compounds of formula (I) include the following:

III.A.

$R^A$ is a leaving group selected from: OH, O-PG, where PG is a protecting group, or $-OSO_2-R^{27}$, wherein $R^{27}$ is selected from p-tolyl, p-bromophenyl, p-nitrophenyl, methyl, trifluoromethyl, perfluorobutyl and 2,2,2-trifluoroethyl;

or $R^A$ is a group of formula II, and

W is N;

$L^0$ is H, $C_{1-6}$ alkyl, $C_{1-6}$ alkoxy, hydroxy, chloro;

$L^1$ and $L^2$ are each independently H, halogen or $C_{1-4}$ alkyl;

$R^{22}$ is H, $C_{1-6}$ thioalkyl, $C_{1-6}$ alkoxy, phenyl or Het selected from the group consisting of:

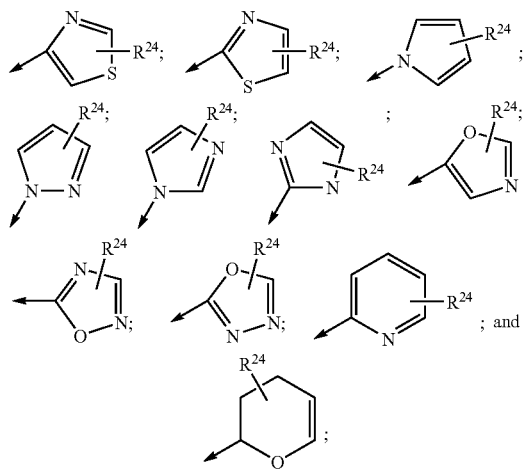

wherein $R^{24}$ is H, $C_{1-6}$ alkyl, $NH-R^{25}$, $NH-C(O)-R^{25}$; $NH-C(O)-NH-R^{25}$, wherein each $R^{25}$ is independently: H, $C_{1-6}$ alkyl, or $C_{3-6}$ cycloalkyl;

or $NH-C(O)-OR^{26}$, wherein $R^{26}$ is $C_{1-6}$ alkyl; or $R^3$ is $NH-C(O)-OR^{20}$, wherein $R^{20}$ is $C_{1-6}$ alkyl, or $C_{3-6}$ cycloalkyl;

D is a 6 to 8 atom saturated or unsaturated alkylene chain optionally containing one or two heteroatoms independently selected from: O, S or $N-R^{28}$, wherein $R^{28}$ is H, $C_{1-6}$ alkyl or $C_{2-7}$ acyl;

$R^4$ is H or $C_{1-6}$ alkyl;

and A is a carboxylic acid or a pharmaceutically acceptable salt or ester thereof.

III.B.

$R^A$ is a leaving group selected from: OH and $-OSO_2-R^{27}$, wherein $R^{27}$ is selected from p-tolyl, p-bromophenyl, p-nitrophenyl, methyl, trifluoromethyl, perfluorobutyl and 2,2,2-trifluoroethyl;

$R^3$ is $NH-C(O)-OR^{20}$, wherein $R^{20}$ is butyl, cyclobutyl or cyclopentyl;

$R^4$ is H or $C_{1-6}$ alkyl;

D is a 7 atom, saturated or unsaturated, all carbon alkylene chain;

A is a carboxylic acid or a pharmaceutically acceptable salt or ester thereof.

III.C.

$R^A$ is $-OSO_2-R^{27}$, wherein $R^{27}$ is p-bromophenyl;

$R^3$ is $NH-C(O)-OR^{20}$, wherein $R^{20}$ is cyclopentyl;

$R^4$ is H;

D is a 7 atom all carbon chain containing one cis double bond at position 13, 14; and $R^B$ is a moiety of the following formula wherein the position 14-cyclopropyl bond is syn to the ester group:

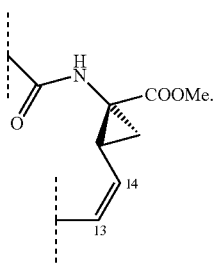

IV. Methods for Synthesizing Compounds of Formula (I)

The compounds of formula (I) may be prepared by the methods as described in the numerous patent documents cited in the above Background Information section and/or by the methods as set forth below. The compounds of formula (I) are preferably prepared via ring-closing olefin metathesis (RCM) reactions in the presence of ruthenium-based catalysts.

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/09543 and WO 00/09558, U.S. Pat. No. 6,323,180 B1 and U.S. Pat. No. 6,608,027 B1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

In particular embodiment, the compounds of formula I set forth below:

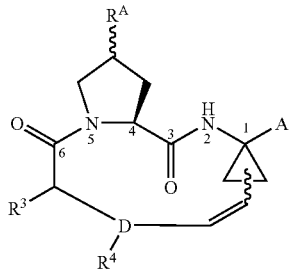

(I)

may be prepared by subjecting a diene compound of formula II

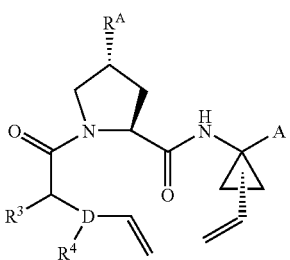

(II)

wherein $R^A$, $R^3$, $R^4$, D and A are as defined hereinbefore;
to a metathesis cyclization reaction in the presence of a ruthenium catalyst;
and when A is a carboxylic acid ester group in the resulting compound of formula (I), optionally subjecting the compound of formula (I) to hydrolysis conditions to obtain a compound of formula (I) wherein A is a carboxylic acid group;
and when A is a carboxylic acid group in the resulting compound of formula (I), optionally coupling this compound with a sulfonamide of formula $R^{5A}SO_2NH_2$ in the presence of a suitable coupling agent, such as TBTU or HATU, to obtain a compound of formula (I) wherein A is —C(O)—NH—$SO_2R^{5A}$.

Suitable ruthenium catalysts for the metathesis cyclization step include any of the well-known ruthenium catalysts useful for RCM reactions, including the compounds of formula IV, V, VI, VII or VIII:

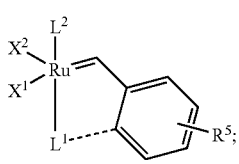

(IV)

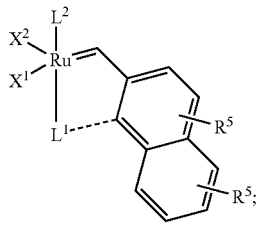

(V)

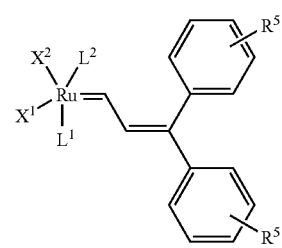

(VI)

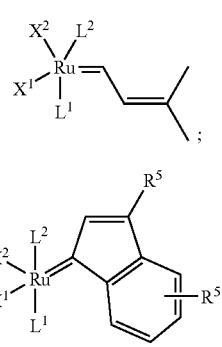

(VII)

(VIII)

wherein
$X^1$ and $X^2$ each independently represent an anionic ligand,
$L^1$ represents a neutral electron donor ligand which is bonded to the ruthenium atom and is optionally bonded to the phenyl group, and
$L^2$ represents a neutral electron donor ligand which is bonded to the ruthenium atom;
and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and
wherein $X^2$ and $L^2$ may optionally together form a chelating bidentate ligand.

In a more specific embodiment, the ruthenium catalyst is a compound of formula (IV-A) or (IV-B):

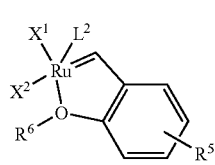

(IV-A)

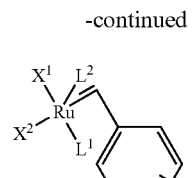

(IV-B)

wherein:

$L^1$ is a trisubstituted phosphine group of the formula $PR_3$, wherein R is selected from $C_{1-6}$alkyl and $C_{3-8}$cycloalkyl, $L^2$ is a trisubstituted phosphine group of the formula $PR_3$, wherein R is selected from $C_{1-6}$alkyl and $C_{3-8}$cycloalkyl, or $L^2$ is a group of the formula A or B:

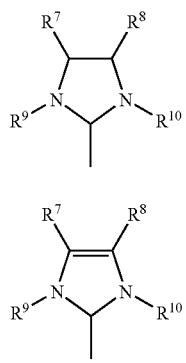

wherein $R^7$ and $R^8$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and $R^9$ and $R^{10}$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$ alkyl, HS—$C_{1-6}$alkyl, HO—$C_{1-6}$alkyl, perfluoro$C_{1-6}$ alkyl, $C_{3-6}$ cycloalkyl, $C_{1-6}$alkoxy, hydroxyl, halogen, nitro, imino, oxo, thio or aryl;

$X^1$ and $X^2$ each independently represent a halogen atom;

$R^5$ represent hydrogen or nitro; and $R^6$ represents a $C_{1-6}$ alkyl group.

In another more specific embodiment, the ruthenium catalyst is selected from:

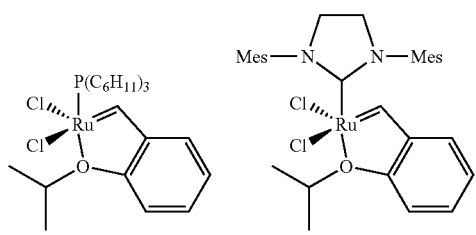

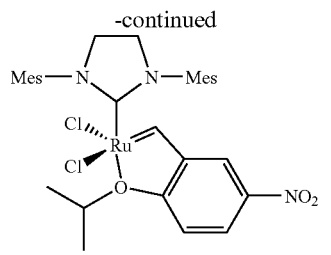

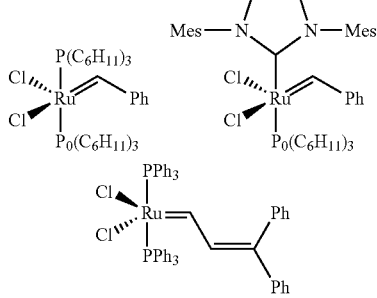

where Ph is phenyl and Mes is 2,4,6-trimethylphenyl.

Ruthenium-based catalysts useful for the metathesis cyclization step, such as those set forth above, are all known catalysts that may be obtained by known synthetic techniques. For example, see the references cited in the Background section above as well as the following references for examples of such ruthenium-based catalysts:

Organometallics 2002, 21, 671; 1999, 18, 5416; and 1998, 17, 2758;

J. Am. Chem. Soc. 2001, 123, 6543; 1999, 121, 791; 1999, 121, 2674; 2002, 124, 4954; 1998, 120, 2484; 1997, 119, 3887; 1996, 118, 100; and 1996, 118, 9606

J. Org. Chem. 1998, 63, 9904; and 1999, 64, 7202;

Angew. Chem. Int. Ed. Engl. 1998, 37, 2685; 1995, 34, 2038; 2000, 39, 3012 and 2002, 41, 4038;

U.S. Pat. Nos. 5,811,515; 6,306,987 B1; and 6,608,027 B1

The metathesis reaction may carried out in the presence of an organic solvent as a diluent in a temperature range from about 40 to about 120° C., preferably from about 60 to about 100° C., in particular at about 80° C. In a preferred embodiment the organic solvent is selected from alkanes, such as n-pentane, n-hexane or n-heptane, aromatic hydrocarbons, such as benzene, toluene or xylene, and chlorinated hydrocarbons such as dichloromethane, trichloromethane, tetrachloromethane or dichloroethane.

In another preferred embodiment the molar ratio of the diene compound of formula II to the catalyst ranges from 1000:1 to 100:1, preferably from 500:1 to 110:1, in particular from 250:1 to 150:1.

In another preferred embodiment the process is carried out at a ratio of the diene compound of formula II to diluent in the range from 1:400 by weight to 1:25 by weight, preferably from 1:200 by weight to 1:50 by weight, in particular from 1:150 by weight to 1:75 by weight.

In another particular embodiment, the compounds of formula IA below:

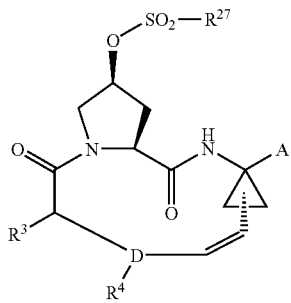

(IA)

wherein $R^3$, $R^4$, $R^{27}$, A and D have the meaning given for formula I, may be prepared by macrocyclizing a diene compound of formula IIA:

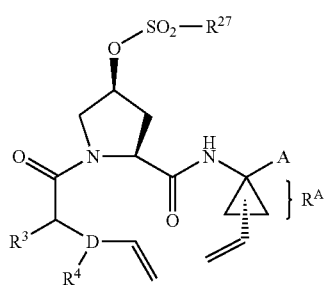

(IIA)

wherein $R^3$, $R^4$, $R^{27}$, D and A are as defined hereinbefore;

in the presence of a ruthenium catalyst.

Suitable conditions and catalysts for the metathesis conversion of diene compound IIA to macrocycle IA include those set forth previously for the metathesis conversion of diene compound II to macrocycle I.

The diene compounds of formula (II) used as a starting materials may be obtained from commercially available materials using the techniques described in U.S. Pat. No. 6,608,027 B1.

The diene compounds of formula (IIA) used as a starting materials may be obtained from commercially available materials using the techniques described in steps (i), (ii) and (iii) below:

Step (i)

This step is directed to a process for preparing a compound of formula (1):

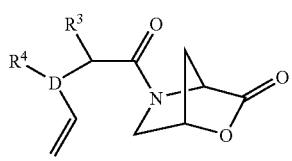

(1)

said process comprising:

reacting a compound of formula (2), or a salt thereof, with a compound of formula (3):

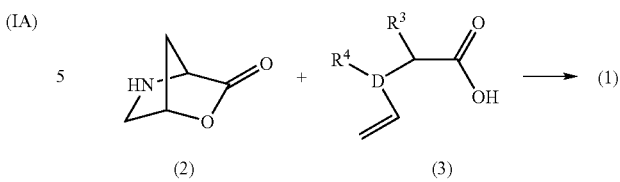

Peptide coupling between compounds of formula (2) and (3) could be obtained under a variety of conditions known in the art using conventional peptide coupling reagents such as DCC, EDC, TBTU, HBTU, HATU, DMTMM, HOBT, or HOAT in aprotic solvents such as dichloromethane, chloroform, DMF, NMP, DMSO.

In a specific embodiment, the compound of formula (2) is used in the form of its mesylate salt.

The cyclic lactone of formula (2), used as starting material can be obtained from a commercially available 4-hydroxyproline compound of formula (4) using standard techniques as outlined in the following general scheme:

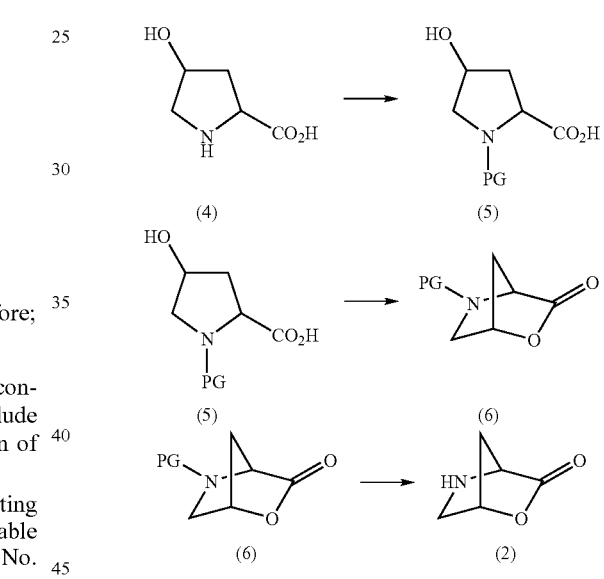

In the first step, an appropriate amino-protecting group is introduced onto the ring nitrogen atom of the 4-hydroxyproline compound of formula (4) using conventional procedures. For example, compound of formula (4) may be dissolved in a suitable solvent and reacted with an appropriate amino-protecting group introducing reagent. For example, and not intending to be limited in its scope, when Boc (tert-butyloxycarbonyl) is the desired protecting group, compound (4) is reacted with the anhydride $Boc_2O$ (or Boc-ON) in a solvent mixture such as Acetone/Water, MIBK/Water, THF/Water to which a base such as NaOH, KOH, LiOH, triethylamine, diisopropylethylamine, or N-methyl-pyrrolidine is added, the reaction being carried out at a temperature between 20–60° C.

In the second step, the protected 4-hydroxyproline compound of formula (5) is converted to the cyclic lactone compound of formula (6) by reaction with an appropriate cyclizing reagent in a suitable solvent. In one embodiment, the OH functionality of the compound of formula (5) is first reacted with an acid chloride (such as methanesulfonyl chloride, p-toluenesulfonyl chloride, or trifluoromethanesulfonyl chloride) in a non-protic solvent (such as THF, dioxane, dichloromethane, chloroform, N-methylpyrrolidone, dimethyl sulfoxide, dimethylformamide, acetone, or methylisobutylketone) in the presence of a tertiary amine base (such as N-methyl-pyrrolidine, diisopropylethylamine or triethylamine) to render a compound with a suitable leaving group, followed by cyclization of the obtained compound in a polar non-protic solvent (such as dioxane) in the presence of a tertiary amine base to give the desired cyclic lactone of formula (6).

In the third step, the cyclic lactone compound of formula (6) is deprotected using conventional deprotection techniques, for example, by heating compound of formula (6) in a suitable solvent in the presence of an acid such as p-toluenesulfonic acid, HCl, HBr, HI, HF, $H_2SO_4$, $H_3PO_4$, methanesulfonic acid or trifluoroacetic acid, to obtain the compound of formula (2).

Compound of formula (2) may optionally be converted into a salt form by reaction with an appropriate acid. A specific example of the preparation of the mesylate salt of compound of formula (2) starting from an appropriate 4-hydroxyproline compound of formula (4) is found in the Synthetic Examples section below.

The substituted acid compound of formula (3) used as a starting material may be obtained from commercially available materials using the techniques described in U.S. Pat. No. 6,608,027 B1.

Step (ii)

Step (ii) is directed to a process for preparing a compound of formula (7):

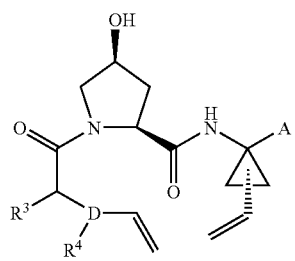

(7)

said process comprising:
reacting a compound of formula (1) with a compound of formula (8):

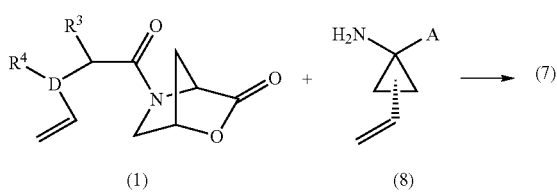

A mixture of compound of formula (1), compound of formula (8) and a suitable base, such as sodium 2-ethylhexanoate (SEH), in a suitable solvent (such as water, toluene, pyridine, a suitable solvent mixture such as toluene/THF or a suitable biphasic solvent system such as water/toluene) is stirred at a temperature from about 20° C. to about 80° C. until completion of the reaction. For work-up the organic layer may be washed and the product isolated after removing the solvent.

The compound of formula (8) used as starting material may be obtained from commercially available materials using the techniques described in International Patent Applications WO 00/09543, WO 00/09558, U.S. Pat. No. 6,323, 180 B1 and U.S. Pat. No. 6,608,027 B1.

Step (iii)

Step (iii) is directed to a process for preparing a compound of formula (IIA):

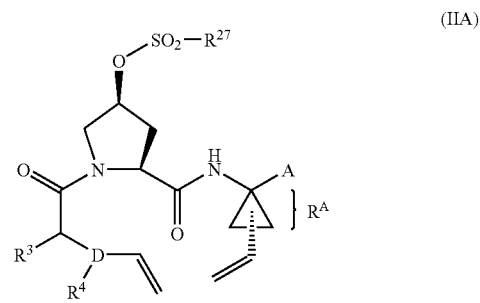

said process comprising:
reacting a compound of formula (7) with a compound of formula (9):

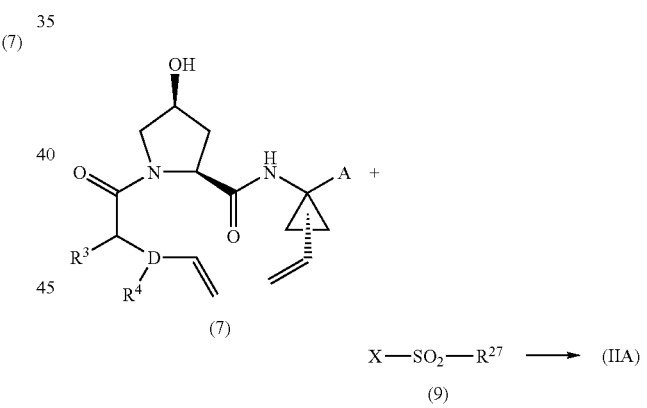

wherein X represents a suitable leaving group and $R^{27}$ is selected from p-tolyl, p-bromophenyl, p-nitrophenyl, methyl, trifluoromethyl, perfluorobutyl and 2,2,2-trifluoroethyl;

To a mixture of compound of formula (7) and an organic base (such as DABCO, triethylamine, 1-methylpyrrolidine or pyridine) in an organic solvent (such as ether, dichloromethane, chloroform or toluene), a solution of the compound of formula (9) is added and the resultant mixture is stirred at ambient temperature (15–25° C.) until completion of reaction.

The following scheme provides another alternative process using known methods for preparing a key compound of formula 1 h from acyclic intermediates:

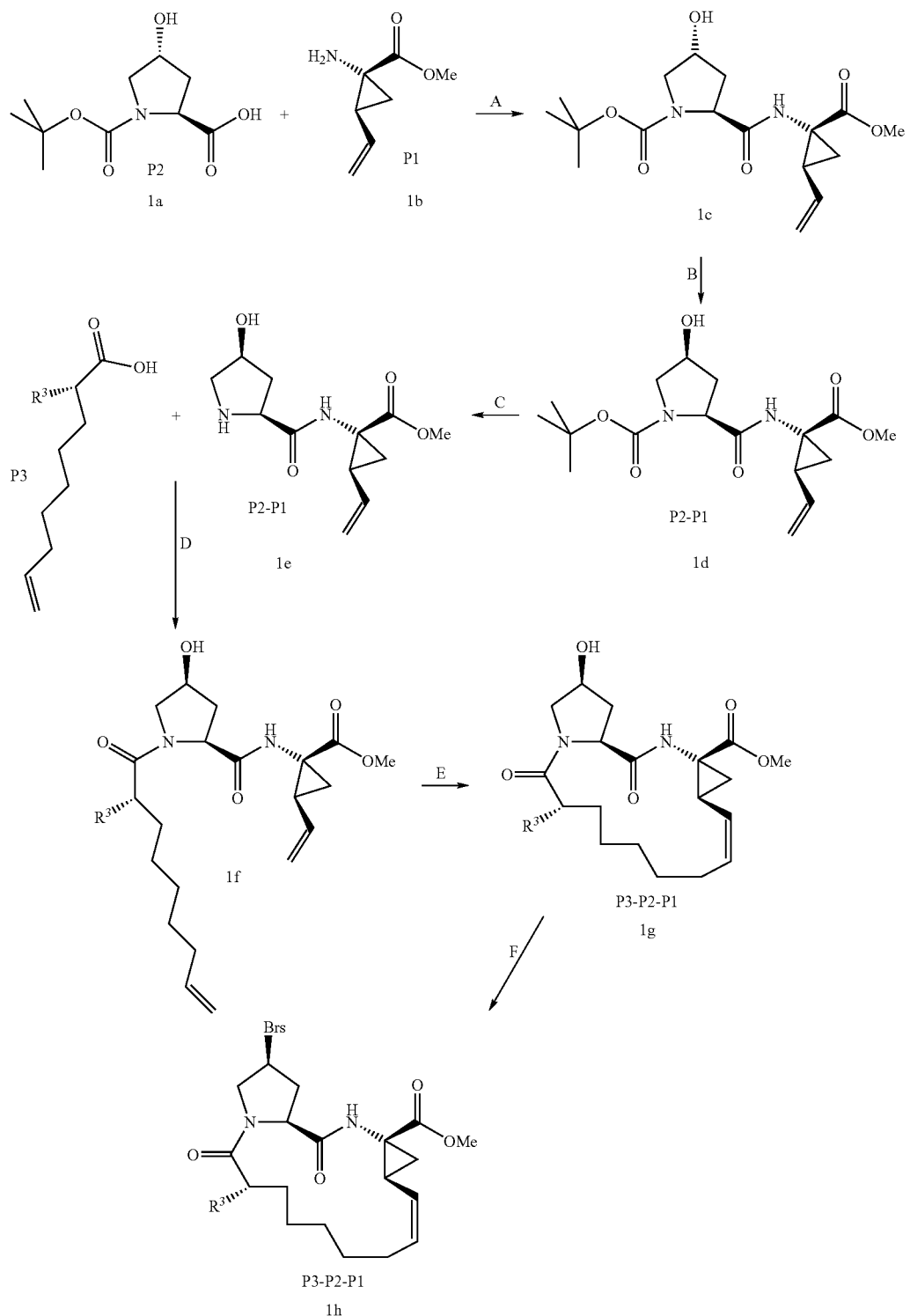

Scheme 1

Scheme I:

Steps A, C, D: Briefly, the P1, P2, and P3 moieties can be linked by well known peptide coupling techniques generally disclosed in WO 00/09543 & WO 00/09558.

Step B: This step involves the inversion of configuration of the 4-hydroxy substituent. There are several ways in which this can be accomplished as will be recognized by persons skilled in the art. One example of a convenient method is the well known Mitsunobu reaction (Mitsunobu Synthesis 1981, January, 1–28; Rano et al. Tet. Lett. 1994, 36, 3779–3792; Krchnak et al. Tet. Lett. 1995, 36, 6193–6196).

Step E: The formation of the macrocycle can be carried out via an olefin metathesis using a ruthenium-based catalyst such as those set forth previously for the metathesis conversion of diene compound II to macrocycle I.

Step F: Conversion of the hydroxyl group of the proline to a suitable leaving group (i.e. brosylate) was carried out by reacting the free OH with the corresponding halo-derivative (i.e. 4-bromobenzenesulfonyl chloride).

Subsequent conversion of the key compound of formula 1 h to other compounds of formula I is described in detail in the examples hereinafter.

In one embodiment, the cyclized compounds of formula IA above can be used to prepare other compounds of formula I wherein $R^4$ is a group of formula II (i.e. the compounds of formula IB below), using the following sequence:

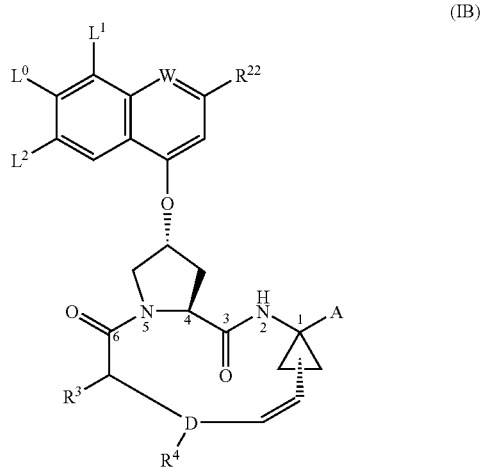

(IB)

the process comprising reacting a macrocyclic compound of formula (IA) with a compound of formula (X):

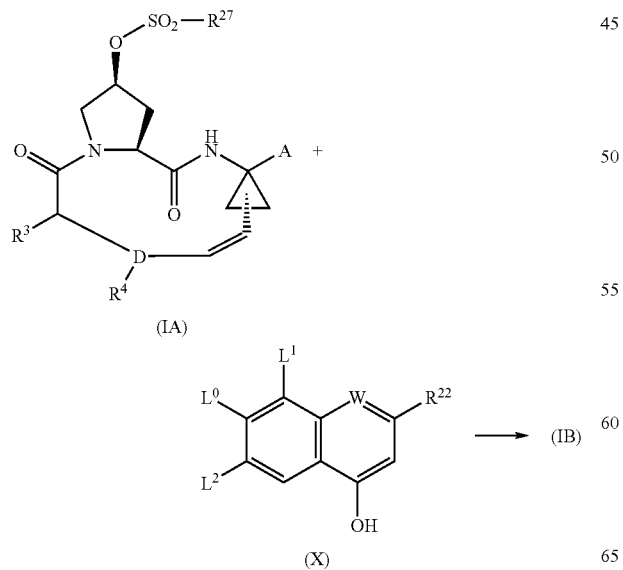

and when A is a carboxylic acid ester group in the resulting compound of formula (IB), optionally subjecting the compound of formula (IB) to hydrolysis conditions to obtain a compound of formula (IB) wherein A is a carboxylic acid group; and when A is a carboxylic acid group in the resulting compound of formula (IB), optionally coupling this compound with a sulfonamide of formula $R^{114}SO_2NH_2$ in the presence of a suitable coupling agent, such as TBTU or HATU, to obtain a compound of formula (IB) wherein A is $-C(O)-NH-SO_2R^{114}$.

Compounds of formula (IA) and (X) are mixed in a polar non-protic organic solvent (such as THF, Dioxane, dicholormethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of reaction. Aqueous workup followed by crystallization from a suitable solvent such as ethylacetate-heptane or ethylacetate/methylcyclohexane provides the compounds of formula (IB).

When A is a carboxylic acid ester group in formula (IB), the esterified compound of formula (IB) can optionally be subjected to hydrolysis conditions to obtain the corresponding free carboxylic acid compound. Hydrolysis can be carried out using conventional hydrolysis conditions known in the art.

The compound of formula (X) used as starting material may be obtained from commercially available materials using the techniques described in International Patent Applications WO 00/09543, WO 00/09558, U.S. Pat. No. 6,323,180 B1 and U.S. Pat. No. 6,608,027 B1.

The compounds of formula I can be subjected to the process of the present invention as the next step after the RCM reaction step forming the cyclized product or after further conversion of the cyclized product to other compounds. For example, the reaction product containing cyclized compound IA can be subjected to the process of the present invention after the RCM of compound IIA to form IA; and/or the reaction product IB can be subjected to the process of the present invention after the further conversion of compound IA to compound IB as set forth above.

V. More Specific Embodiments of the Process

The following are additional specific embodiment of the process of the present invention:

A process for removing ruthenium or ruthenium-containing compound from a mixture comprising: (i) a compound of the following formula I:

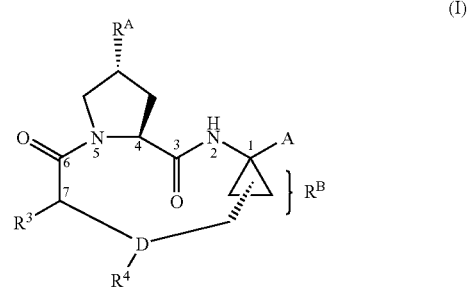

wherein

R⁴ is —OSO₂—R²², wherein R²² is p-bromophenyl;
R³ is NH—C(O)—OR²⁰, wherein R²⁰ is cyclopentyl;
R⁴ is H;
D is a 7 atom all carbon chain containing one cis double bond at position 13, 14; and R^B is a moiety of the following formula wherein the position 14-cyclopropyl bond is syn to the ester group:

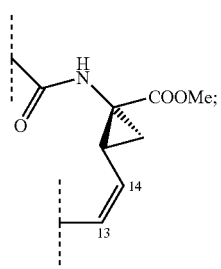

(ii) an organic solvent; and (iii) ruthenium or ruthenium-containing compound;
said process comprising:

(1) exposing said mixture to pressurized carbon dioxide at a temperature of about 30 to 150° C. and at a pressure of about 74 to 500 bar to form a solution comprising carbon dioxide, the compound of formula (I) and the organic solvent, such that particles of the ruthenium or ruthenium-containing compound precipitate out of said solution;

(2) introducing the solution into a lower pressure region to expel at least some of the carbon dioxide from the solution and obtain an organic solvent solution comprising the compound of formula (I) and the organic solvent;

(3) optionally repeating steps (1) and (2) one or more times using the organic solvent solution obtained in step (2) as the mixture to be exposed in step (1) to said pressurized carbon dioxide; and (4) optionally recovering the compound of formula (I) from the organic solvent solution.

A process as set forth above, wherein the mixture is exposed to the pressurized carbon dioxide by injecting the mixture into a vessel containing the pressurized carbon dioxide and the amount of carbon dioxide in the resulting solution is in the range of about 80 to 99%.

A process as set forth above, wherein the level of ruthenium in the recovered compound of formula (I) is less than about 1000 ppm, for example, less than about 300 ppm, for example, less than about 100 ppm, for example, less than about 60 ppm.

The following examples set forth techniques demonstrating various aspects of the present invention. It is to be understood, however, that these examples are presented by way of illustration only and that nothing therein should be taken as a limitation upon the overall scope of the present invention.

EXAMPLES

Example 1

Preparation of a Brosylated Diene Intermediate 1

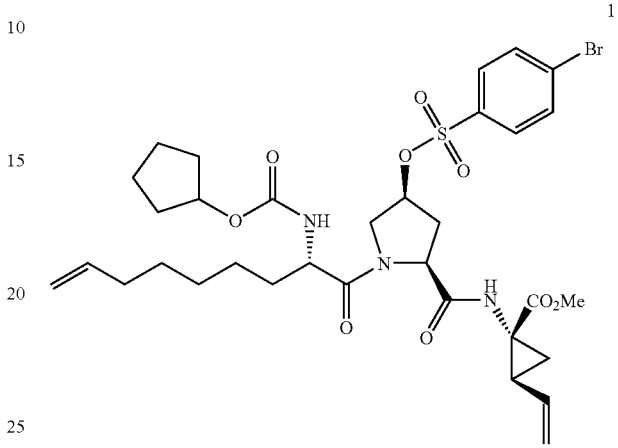

Step 1: Introduction of the Boc-Protecting Group: Synthesis of (2)

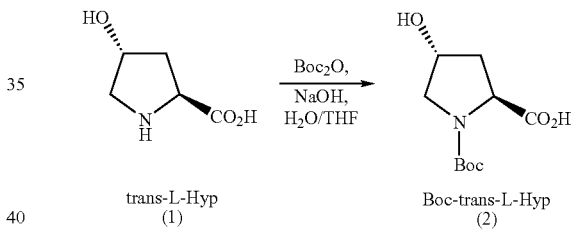

The amino-protection was done with the Boc-protecting-group. (1) (trans-4-hydroxy L-proline) (249.8 g, 1.905 mol) was dissolved in water (375 ml) and 45% sodium hydroxide solution (203 g, 2.286 mol). To ensure good phase transfer, tert-butanol (106 g) was added. In a different procedure, acetone was used instead of THF/tert-butanol. The reaction mixture was heated to 50° C. and the anhydride Boc₂O (424 g, 1.943 mol) was dissolved in THF (425 ml, or acetone) is slowly added. The reaction is exothermic and generates gas (CO₂) as the Boc₂O was added. If the reaction does not proceed as wanted, catalytic amounts of DMAP (2.3 g, 19 mmol) can be added. After the addition of the Boc₂O, the reaction mixture is kept ½–1 h at 50° C., and the THF was removed by partial distillation. The pH of the remaining solution was adjusted to about pH3 with concentrated HCl (204 g, 2.076 mol) and the product was then extracted with MIBK (1 liter) and again with MIBK (375 ml). The organic layer was heated and some of the solvent was distilled off to remove traces of water. The product was crystallized from this solution by adding MCH (1.25 l), isolated by filtration, washed twice with MCH (375 ml) and dried overnight at 40° C.

Yield: 77–78%, colorless crystals, $F_p$=126–128° C.

Step 2: Formation of the Lactone: Synthesis of (3)

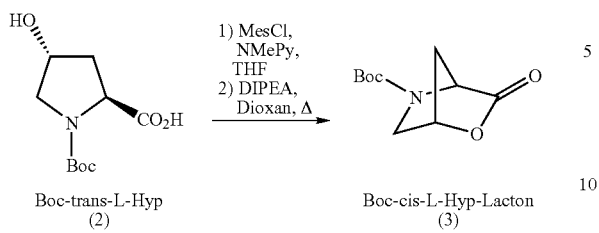

Boc-trans-L-Hyp (2)   Boc-cis-L-Hyp-Lacton (3)

(2) (416.3 g, 1.8 mol) is dissolved in THF (2.08 l) and cooled with ice to a temperature from about −5–to about −10° C. Mesylchloride (392 g, 3.4 mol) and N-Methylpyrrolidine (429 g, 5 mol) is added and the mixture stirred for about 1½ h at about −5° C. The mixture is washed with water and heated up to reflux. Dioxane (2.08 l) is poured in and the THF is distilled off. After cooling down to room temperature, DIPEA (233 g, 1.8 mol) is added and the mixture is heated to reflux. After 1 h part of the solvent (830 ml) is distilled off, cooled to ambient temperature and a KHSO$_4$-solution (14.4 g in 2.08 l water) is poured in and the solution is allowed to cool down to room temperature. The resulting crystals are isolated by filtration, washed with water and dried overnight at 45° C.

Yield: 78–82%, colorless needles, $F_p$=111° C.

Step 3: Deprotection of the Lactone; Synthesis of (4)

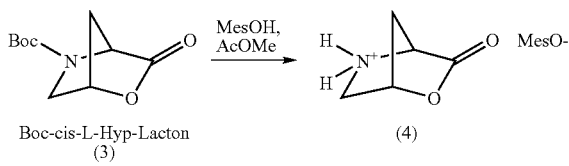

Boc-cis-L-Hyp-Lacton (3)   (4)

The lactone (3) (267 g, 1.25 mol) is dissolved in Methylisobutylketone (1467 ml). The suspension is heated up to 50° C. until the lactone is completely dissolved and a part of the solvent (130 ml) is distilled off to remove traces of water. Methansulfonic acid (240 g, 2.5 mol) is added slowly to the reaction mixture. During the addition gas is evolved (CO$_2$, Isobutene). The reaction mixture is allowed to cool to room temperature and the resulting crystals are isolated by filtration, washed twice with acetone (each 400 ml) and dried overnight at 40° C.

Yield: 93–98%, colorless crystals, 208–210° C.

Step 4: Coupling with (5); Synthesis of the Dipeptide (6)

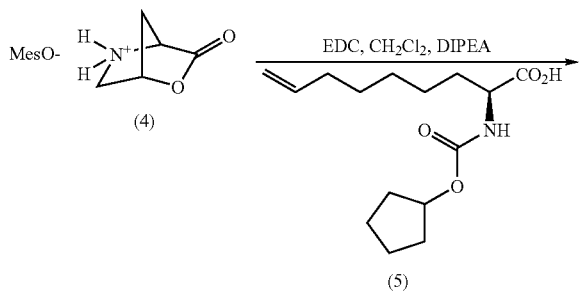

-continued

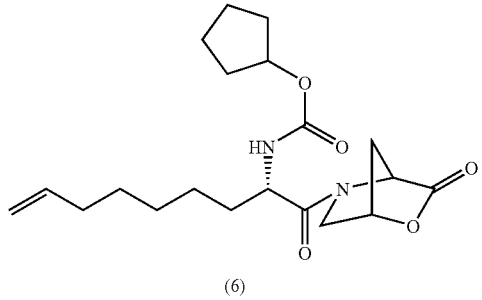

(6)

Compound (5) may optionally be obtained by releasing it from a salt form of the compound. For example, if a DCHA salt form is used (5)·DCHA (61.4 g, 132 mmol) is dissolved in toluene (160 ml) and the resulting solution is washed with diluted sulfuric acid (5.3 g in 80 ml water) and water (80 ml). After phase separation, the solution is treated with charcoal and filtered and the resulting solution stored at room temperature.

The deprotected lactone (4) (24.9 g, 119 mmol) and EDC.HCl (26.8 g, 140 mmol) are suspended in dichloromethane (140 ml) and cooled to room temperature. The suspension is treated with the (5)-solution generated before. To this suspension, di-isopropylethylamine (Hünigs-Base, 16.3 g, 130 mmol) is slowly added while the reaction is kept under nitrogen at temperatures below 20° C. The suspension is filtered, and the resulting solution is washed water (80 ml), diluted acetic acid (1.3 g in 80 ml water), 5% sodium bicarbonate solution (80 ml) and again with water (80 ml). After phase separation, dichloromethane is distilled off under reduced pressure. The resulting solution can directly be used for the next step. Otherwise, the product can be isolated by crystallization from MCH.

Yield: 95% (GC), yellowish solution, $F_p$=58–60° C.

Step 5: Synthesis of (8)

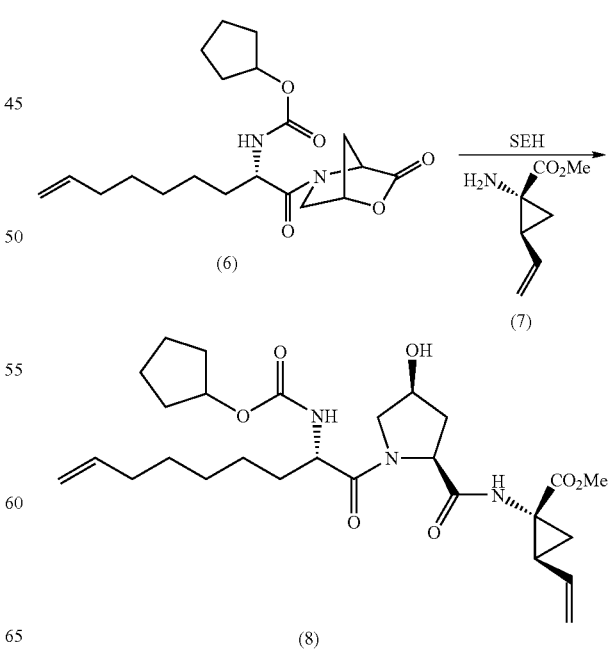

A mixture of (6) (10.0 g, 23.7 mmol, 1.0 eq.), (7) (7.6 g, 24.2 mmol, 1.02 eq.) and sodium 2-ethylhexanoate (SEH) (5.9 g, 35.6 mmol, 1.5 eq.) in water (43 ml) and toluene (12 ml) is stirred at 80° C. for 2 h. For work-up toluene (75 ml) is added at 80° C. After stirring and separation of the aqueous layer, the organic layer is washed with 1M Na₂CO₃ (3×30 ml), 0.5M HCl (30 ml) and water (2×30 ml). The solvent is removed under vacuum.

Yield of (8): 11.7 g, 22.5 mmol, 95%; purity: >95% (peak-area HPLC) as a slightly yellow oil.

Step 6. Brosylation of (8); Synthesis of 1

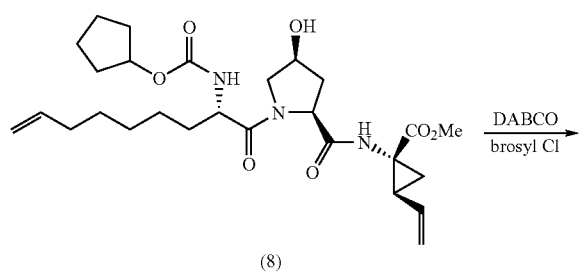

(8)

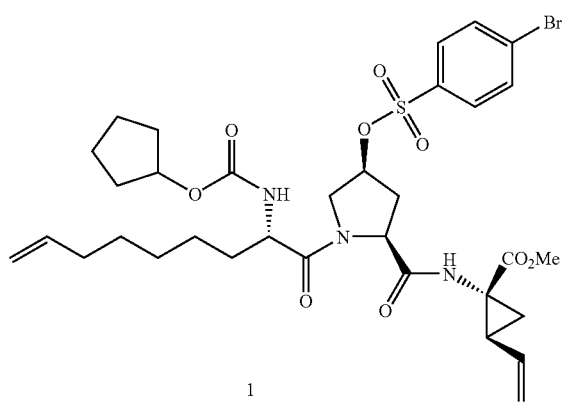

1

To a mixture of (8) (10.7 g, 18.5 mmol, 1.0 eq.) and DABCO (3.3 g, 29.7 mmol, 1.6 eq.) and toluene (23 ml) a solution of 4-bromobenzenesulfonyl chloride (brosyl chloride, 6.6 g, 26.0 mmol, 1.4 eq.) in toluene (15 ml) is added slowly at room temperature. The mixture is stirred for 2 h. For work-up the organic layer is washed with 1M Na₂CO₃ (2×21 ml), diluted with THF (21 ml) and washed with 0.5M HCl (21 ml) and water (2×21 ml). The solvent is removed under vacuum.

Yield of (9): 12.3 g, 16.7 mmol, 90%; purity: >95% (peak-area HPLC) as a slightly orange oil. A charcoal treatment of the crude product is possible.

Example 2

Procedure for Single Run Extraction of RCM Reaction Mixture

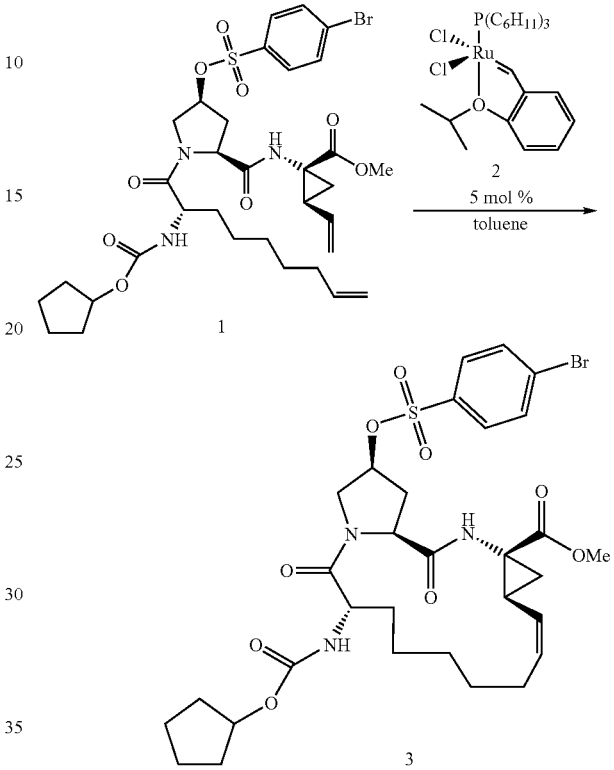

Compound 1 (g) was dissolved in toluene at a concentration of 0.01 M and 5 mol % of ruthenium catalyst 2 was added. The reaction was stirred at 70° C. for 24 hours. A portion of the resulting reaction mixture (81 g) was then placed into a 1 L pressure reactor. The reactor was heated to 40° C. and CO₂ was introduced to obtain a pressure of 96.5 bar. The mixture was allowed to equilibrate under these conditions for ~30 min, then the vessel outlet was cautiously opened and the efflux was led through inert tubing at a rate of about 1.5 mL/min into a collection flask that was cooled at 0° C. Three fractions of roughly equal volume were recovered. The organic extracts were concentrated and the residue was dried under high vacuum to give the product 3 as an amorphous solid (three fractions). The total recovery was ~90% based on the mass of concentrated recovered material. The three fractions contained almost exclusively the desired cyclized product 3. HPLC (220 nM) showed purity of the desired product was >99%, (less than 1% unwanted dimers or other by-products). For comparison, HPLC of the crude reaction mixture indicated about 85% purity of the desired product. ICP-MS analysis (Inductive-coupled plasma mass spectroscopy, see H. D. Maynard and R. H. Grubbs, Tetrahedron Lett, 1999, 40, 4137, reference 11) indicated a level of ruthenium of 56 ppm in the recovered product 3.

The solid recovered in the reactor was highly colored and contained mostly recovered catalyst 2 along with dimer side-products from the cyclization and catalyst by-products.

The recovered catalyst mixture was recycled in a new metathesis reaction and functioned well as a catalyst (~95% conversion after 36 h).

Example 3

Procedure for Continuous Extraction of RCM Reaction Mixture

A pressure reactor equipped and set up for supercritical fluid extraction (see U.S. Pat. No. 6,294,194, incorporated herein by reference) was equipped with 0.5 micron porous filters at the inlet and outlet. The vessel set at 40° C. and was charged with $CO_2$ to a pressure of 137.9 bar and a continuous flow of 100 mL/min was maintained. Crude metathesis reaction mixture (1,000 mL; obtained using the same procedure as Example 2) was injected continuously at 5 mL/min through a separate inlet. The efflux was led through inert tubing at a rate of 5 mL/min into a collection flask, cooled at 0° C., and allowed to degas. After a total of 1,000 mL of reaction solution was injected, the collected efflux was allowed to completely degas and was then concentrated and the residue was dried under high vacuum. HPLC (220 nM) of the residue showed product 3, >98% pure with <2% unwanted dimers or other by-products present. Recovery of 3 was >95%. ICP-MS analysis indicated a Ru level of 839 ppm.

Example 4

Procedure for Continuous Extraction with Added Lactose

The procedure was repeated in the same manner as Example 2, except the reactor was first charged with lactose (5–10 micron particle size, 10% by weight of the weight of the injected reaction solution). The reaction product was isolated as in Example 2 and ICP-MS analysis found 668 ppm Ru.

Diatomaceous earth may also be used in place of lactose to reduce the amount of Ru in the product. The amount of Ru in the product may also be modulated by adjusting the flow rate of the process.

Example 5

Possible Subsequent Transformations of Compound 3

Step 1: Synthesis of (12):

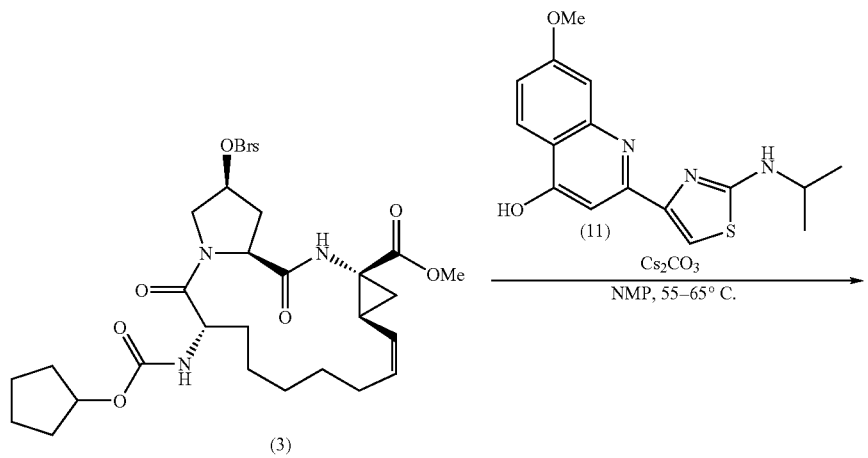

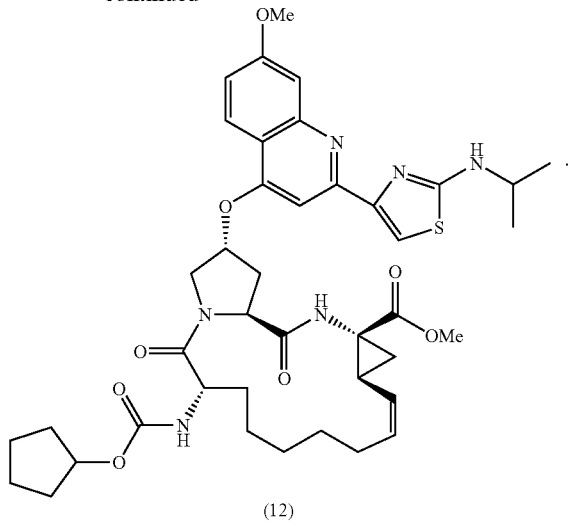

(12)

A mixture of (3) (1 eq.), Cs$_2$CO$_3$ (1 eq.), and (11) (1 eq.) in NMP is stirred for 8 h at 55 to 65° C. After completion of the reaction the mixture is diluted with ethylacetate and washed with 2.5% NaHCO$_3$ solution. The organic layer is extracted three times with a mixture of a 2.5% solution of NaHCO$_3$ and NMP. The organic layer is treated with charcoal, filtered, and the product is crystallised by the addition of n-heptane (or methylcyclohexane). The suspension is cooled to 5° C., the precipitate is filtered and washed with ethylacetate/n-heptane (or ethylacetate/methylcyclohexane) and dried in vacuo.

Yield: 60–70%, white crystals.

If necessary, the product can be recrystallised from ethylacetate/methylcyclohexane.

Step 2: Synthesis of Compound #822 (An HCV Inhibitor Compound):

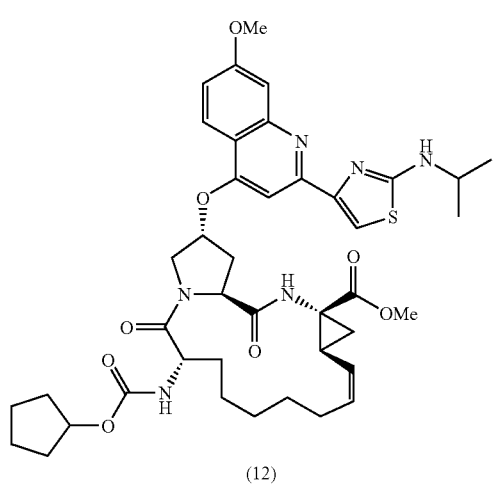

(12)

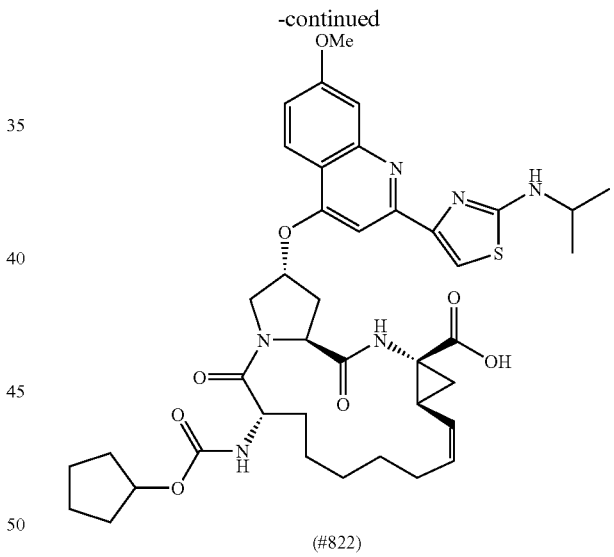

(#822)

20 g (0.025 mol) of (12) is dissolved in 160 ml of THF and 2.45 g (0.0583 mmol) of LiOH.H$_2$O is added to the solution. After the addition of 54 ml of water the reaction mixture is stirred for at least 8 h at a temperature of 40–45° C. After complete conversion (HPLC) the biphasic system is cooled to 20–25° C. After separation of the layers (a small aqueous phase is separated) 54 ml of ethanol is added to the organic layer and the pH is adjusted to pH 5.5–5.7 by the addition of 1M HCl solution. The mixture is warmed to 40–45° C. and 80 ml of water are added over a period of at least 30 min (40–45° C.). During this procedure the solution becomes cloudy. The mixture is stirred for further 60 min at a temperature of 40–45° C. (after 15 min the product should precipitate). Further 80 ml of water are added at 40–45° C. over a period of at least 30 min and the mixture is stirred for another 60 min at the same temperature. The suspension is cooled to 20–25° C. and stirred at this temperature for 1 h. After filtration the precipitate is washed three times by 20 ml of water and dried in vacuo at 35° C. (slight stream of $N_2$).

yield: 17.7–18.7 g of (#822) crude (90–95%)

The product contains between 3 and 5% of water.

We claim:

1. A process for removing ruthenium or ruthenium-containing compound from a mixture comprising: (i) a compound of the following formula (I):

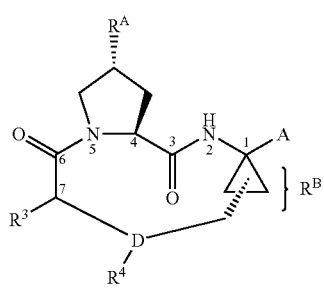

(I)

wherein $R^A$ is a leaving group or a group of formula II

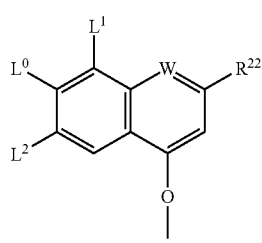

(II)

W is CH or N, $L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state); or $L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring) —$CH_2$— groups not being directly bonded to each other, may be replaced each independently by —O— or $NR^a$ wherein $R^a$ is H or $C_{1-4}$alkyl, and wherein said ring is optionally mono- or di-substituted with $C_{1-4}$ alkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or}$ $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$; or NH—C(O)—NH—$R^{25}$, wherein each $R^{25}$ is independently: H, $C_{1-6}$ alkyl or $C_{3-6}$ cycloalkyl;

or $R^{24}$ is NH—C(O)—$OR^{26}$ wherein $R^{26}$ is $C_{1-6}$ alkyl or $C_{3-6}$ cycloalkyl;

$R^3$ is hydroxy, $NH_2$, or a group of formula —NH—$R^9$, wherein $R^9$ is $C_{6\ or\ 10}$ aryl, heteroaryl, —C(O)—$R^{20}$, —C(O)—NHR$^{20}$ or —C(O)—$OR^{20}$, wherein $R^{20}$ is $C_{1-6}$ alkyl or $C_{3-6}$ cycloalkyl;

D is a 5 to 10 atom saturated or unsaturated alkylene chain optionally containing one to three heteroatoms independently selected from: O, S or N—$R^{27}$, wherein $R^{27}$ is H, $C_{1-6}$alkyl, $C_{3-6}$cycloalkyl or C(O)$R^{28}$, wherein $R^{28}$ is $C_{1-6}$alkyl, $C_{3-6}$cycloalkyl or $C_{6\ or\ 10}$ aryl;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula —C(O)—NH—$R^{11}$, wherein $R^{11}$ is selected from the group consisting of: $C_{1-8}$ alkyl, $C_{3-6}$ cycloalkyl, $C_{6\ or\ 10}$ aryl, $C_{7-16}$ aralkyl, or $SO_2R^{5A}$ wherein $R^{5A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

(ii) an organic solvent; and (iii) ruthenium or ruthenium-containing compound;

said process comprising:

(1) exposing said mixture to a sufficient quantity of pressurized gaseous fluid to form a fluid solution in which the compound of formula (I) and organic solvent are substantially soluble but said ruthenium or ruthenium-containing compound is substantially insoluble such that particles of the ruthenium or ruthenium-containing compound precipitate out of said solution;

(2) introducing the fluid solution into a lower pressure region to expel at least some of said gaseous fluid from the fluid solution and obtain an organic solvent solution comprising the compound of formula (I) and the organic solvent;

(3) optionally repeating steps (1) and (2) one or more times using the organic solvent solution obtained in step (2) as the mixture to be exposed in step (1) to said pressurized gaseous fluid; and (4) optionally recovering the compound of formula (I) from the organic solvent solution.

2. A method according to claim 1, wherein the gaseous fluid has a critical temperature of less than about 200° C. and a critical pressure of less than about 689 bar.

3. A method according to claim 1, wherein the gaseous fluid is selected from carbon dioxide, nitrous oxide, trifluoromethane, ethane, ethylene, propane, sulfur hexafluoride, propylene, butane, isobutane, pentane, and mixtures thereof.

4. A method according to claim 1, wherein the gaseous fluid is carbon dioxide.

5. A method according to claim 1, wherein step (1) is conducted at a temperature in the range of about 0.8 to 2.0 times the critical temperature of the gaseous fluid in degrees Kelvin, and at a pressure in the range of about 0.5 to 30 times the critical pressure of the gaseous fluid.

6. A method according to claim 1, wherein step (1) is conducted at a temperature in the range of about 1.0 to 1.1 times the critical temperature of the gaseous fluid in degrees Kelvin, and at a pressure in the range of about 1 to 10 times the critical pressure of the gaseous fluid.

7. A method according to claim 1, wherein step (1) the gaseous fluid is carbon dioxide and the step is conducted at a temperature of about 30 to 150° C. and at a pressure of about 74 to 500 bar.

8. A method according to claim 1, wherein in step (1) the mixture is exposed to the pressurized gaseous fluid by either (a) introducing the gaseous fluid into a vessel containing the mixture or (b) introducing the mixture into a vessel containing the gaseous fluid.

9. A method according to claim 8, wherein the mixture is exposed to the pressurized gaseous fluid by injecting the mixture into a vessel containing the gaseous fluid.

10. A method according to claim 1, wherein in step (1) the amount of gaseous fluid in the resulting fluid solution is in the range of about 50 to 99.9%.

11. A method according to claim 1, wherein in step (1) the amount of gaseous fluid in the resulting fluid solution is in the range of about 80 to 99.9%.

12. A method according to claim 1, wherein step (1) is conducted in the presence of a bed of carrier material capable of retaining precipitated particles of ruthenium or ruthenium-containing compound.

13. A method according to claim 1, wherein the pressure in the lower pressure region of step (2) is at about ambient pressure.

14. A method according to claim 1, wherein steps (1) and (2) are repeated one or more times using the organic solvent solution obtained in step (2) as the mixture to be exposed to said pressurized gaseous fluid in step (1).

15. A method according to claim 1, wherein in step (4), the compound of formula (I) is recovered by distillation or precipitation.

16. A method according to claim 1, wherein the level of ruthenium in the recovered compound of formula (I) is less than about 10000 ppm.

17. A method according to claim 1, wherein the level of ruthenium in the recovered compound of formula (I) is less than about 1000 ppm.

18. A method according to claim 1, wherein the level of ruthenium in the recovered compound of formula (I) is less than about 300 ppm.

19. A method according to claim 1, wherein the level of ruthenium in the recovered compound of formula (I) is less than about 100 ppm.

20. A method according to claim 1, wherein the level of ruthenium in the recovered compound of formula (I) is less than about 60 ppm.

21. A method according to claim 1, wherein:
$R^A$ is a leaving group selected from: OH, O-PG, where PG is a protecting group, or —OSO$_2$—R$^{27}$, wherein R$^{27}$ is selected from p-tolyl, p-bromophenyl, p-nitrophenyl, methyl, trifluoromethyl, perfluorobutyl and 2,2,2-trifluoroethyl;
or $R^A$ is a group of formula II, and
W is N;
$L^0$ is H, $C_{1-6}$ alkyl, $C_{1-6}$ alkoxy, hydroxy, chloro;
$L^1$ and $L^2$ are each independently H, halogen or $C_{1-4}$alkyl;
$R^{22}$ is H, $C_{1-6}$ thioalkyl, $C_{1-6}$ alkoxy, phenyl or Het selected from the group consisting of:

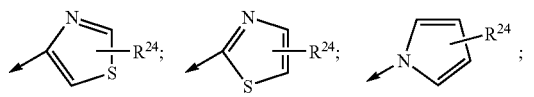

-continued

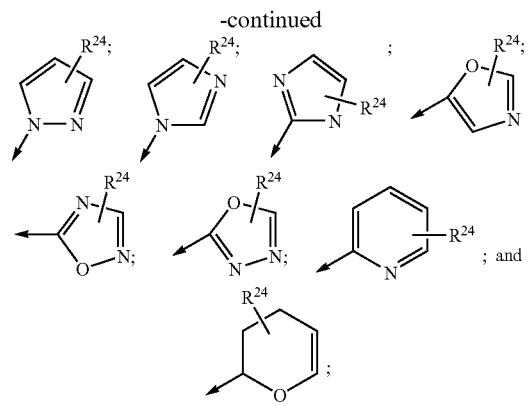

wherein $R^{24}$ is H, $C_{1-6}$ alkyl, NH—R$^{25}$, NH—C(O)—R$^{25}$; NH—C(O)—NH—R$^{25}$, wherein each R$^{25}$ is independently: H, $C_{1-6}$ alkyl, or $C_{3-6}$ cycloalkyl;
or NH—C(O)—OR$^{26}$, wherein R$^{26}$ is $C_{1-6}$ alkyl;
$R^3$ is NH—C(O)—OR$^{20}$, wherein $R^{20}$ is $C_{1-6}$ alkyl, or $C_{3-6}$ cycloalkyl;
D is a 6 to 8 atom saturated or unsaturated alkylene chain optionally containing one or two heteroatoms independently selected from: O, S or N—R$^{28}$, wherein R$^{28}$ is H, $C_{1-6}$alkyl or $C_{2-7}$acyl;
$R^4$ is H or $C_{1-6}$ alkyl;
and A is a carboxylic acid or a pharmaceutically acceptable salt or ester thereof.

22. A method according to claim 1, wherein:
$R^A$ is a leaving group selected from: OH and —OSO$_2$—R$^{27}$, wherein R$^{27}$ is selected from p-tolyl, p-bromophenyl, p-nitrophenyl, methyl, trifluoromethyl, perfluorobutyl and 2,2,2-trifluoroethyl;
$R^3$ is NH—C(O)—OR$^{20}$, wherein R$^{20}$ is butyl, cyclobutyl or cyclopentyl;
$R^4$ is H or $C_{1-6}$ alkyl;
D is a 7 atom, saturated or unsaturated, all carbon alkylene chain;
A is a carboxylic acid or a pharmaceutically acceptable salt or ester thereof.

23. A method according to claim 1, wherein:
$R^A$ is —OSO$_2$—R$^{27}$, wherein R$^{27}$ is p-bromophenyl;
$R^3$ is NH—C(O)—OR$^{20}$, wherein R$^{20}$ is cyclopentyl;
$R^4$ is H;
D is a 7 atom all carbon chain containing one cis double bond at position 13,14; and $R^B$ is a moiety of the following formula wherein the position 14-cyclopropyl bond is syn to the ester group:

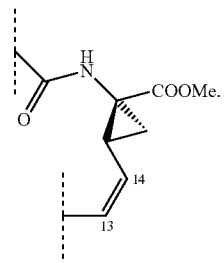

24. A method according to claim 1, wherein the organic solvent is selected from toluene, dichloromethane, THF, dioxane, ethyl acetate, tert-butyl acetate, methyl-tert-butyl ether, methanol, water and mixtures thereof.

25. A process according to claim 1 for removing ruthenium or ruthenium-containing compound from a mixture comprising: (i) a compound of the following formula I:

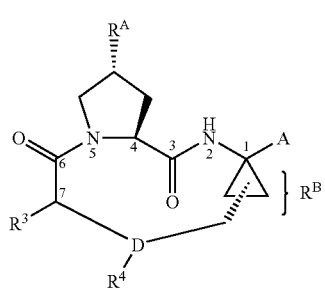

wherein
- $R^A$ is —$OSO_2$—$R^{27}$, wherein $R^{27}$ is p-bromophenyl;
- $R^3$ is NH—C(O)—$OR^{20}$, wherein $R^{20}$ is cyclopentyl;
- $R^4$ is H;
- D is a 7 atom all carbon chain containing one cis double bond at position 13,14; and $R^B$ is a moiety of the following formula wherein the position 14-cyclopropyl bond is syn to the ester group:

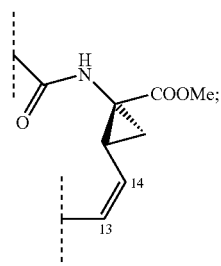

(ii) an organic solvent; and
(iii) ruthenium or ruthenium-containing compound;
said process comprising:
(1) exposing said mixture to pressurized carbon dioxide at a temperature of about 30 to 150° C. and at a pressure of about 74 to 500 bar to form a solution comprising carbon dioxide, the compound of formula (I) and the organic solvent, such that particles of the ruthenium or ruthenium-containing compound precipitate out of said solution;
(2) introducing the solution into a lower pressure region to expel at least some of the carbon dioxide from the solution and obtain an organic solvent solution comprising the compound of formula (I) and the organic solvent;
(3) optionally repeating steps (1) and (2) one or more times using the organic solvent solution obtained in step (2) as the mixture to be exposed in step (1) to said pressurized carbon dioxide; and
(4) optionally recovering the compound of formula (I) from the organic solvent solution.

26. A method according to claim 25, wherein the mixture is exposed to the pressurized carbon dioxide by injecting the mixture into a vessel containing the pressurized carbon dioxide and the amount of carbon dioxide in the resulting solution is in the range of about 80 to 99%.

27. A method according to claim 25, wherein the level of ruthenium in the recovered compound of formula (I) is less than about 1000 ppm.

28. A method according to claim 25, wherein the level of ruthenium in the recovered compound of formula (I) is less than about 300 ppm.

29. A method according to claim 25, wherein the level of ruthenium in the recovered compound of formula (I) is less than about 100 ppm.

30. A method according to claim 25, wherein the level of ruthenium in the recovered compound of formula (I) is less than about 60 ppm.

* * * * *